US010597515B2

(12) United States Patent
Nesvadba et al.

(10) Patent No.: US 10,597,515 B2
(45) Date of Patent: Mar. 24, 2020

(54) POLYCYCLIC GLYOXYLATES AS PHOTOINITIATORS

(71) Applicant: IGM GROUP B.V., Waalwijk (NL)

(72) Inventors: Peter Nesvadba, Marly (CH); Jürgen Baro, Esslingen (DE); Barbara Winkler, Loerrach (DE); Andre Fuchs, Schliengen-Obereggenen (DE)

(73) Assignee: IGM GROUP B.V., RM Waalwijk (NL)

( * ) Notice: Subject to any disclaimer, the term of this patent is extended or adjusted under 35 U.S.C. 154(b) by 0 days.

(21) Appl. No.: 16/325,691

(22) PCT Filed: Aug. 31, 2017

(86) PCT No.: PCT/EP2017/071838
§ 371 (c)(1),
(2) Date: Feb. 14, 2019

(87) PCT Pub. No.: WO2018/041935
PCT Pub. Date: Mar. 8, 2018

(65) Prior Publication Data
US 2019/0211184 A1 Jul. 11, 2019

(30) Foreign Application Priority Data
Sep. 2, 2016 (EP) .................... 16187019

(51) Int. Cl.
*C08K 5/12* (2006.01)
*C07D 307/91* (2006.01)
(Continued)

(52) U.S. Cl.
CPC .............. *C08K 5/12* (2013.01); *C07D 307/91* (2013.01); *C07D 309/32* (2013.01);
(Continued)

(58) Field of Classification Search
CPC ........ C08K 5/12; C08K 5/1545; C08K 5/159; C08K 5/46; C08K 5/1535; C08K 5/101;
(Continued)

(56) References Cited

U.S. PATENT DOCUMENTS 3,989,841 A    11/1976 Stiller et al.
4,038,164 A    7/1977 Via
(Continued)

FOREIGN PATENT DOCUMENTS

DE    2145650 A1    3/1973
DE    2308830 A1    7/1973
(Continued)

OTHER PUBLICATIONS

Machine English translation of JP 63-159379 (Year: 1988).*
(Continued)

*Primary Examiner* — Jessica M Roswell
(74) *Attorney, Agent, or Firm* — Tarolli, Sundheim, Covell & Tummino LLP

(57) ABSTRACT

The present invention relates to photoinitiator compounds of the formula (1) wherein X is O, S or a direct bond; Y is O, S or $CR_9R_{10}$; $R_1$, $R_2$, $R_3$, $R_4$, $R_5$, $R_6$, $R_7$ and $R_8$ independently of each other are hydrogen, halogen, $C_1$-$C_{18}$alkyl, $C_5$-$C_{10}$cycloalkyl, $C_2$-$C_{18}$alkenyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (2) provided that one or more than one of $R_1$, $R_2$, $R_3$, $R_4$, $R_5$, $R_6$, $R_7$ or $R_8$ is a group of formula (2); $R_9$, $R_{10}$ independently of each other are hydrogen, $C_1$-$C_{18}$alkyl, $C_2$-$C_{12}$alkenyl, $C_5$-$C_{10}$cycloalkyl, phenyl-$C_1$-$C_4$alkyl, phenyl or together with the C atom to which they are attached form a 5-membered, 6-membered or 7-mem-
(Continued)

bered ring; and $R_{11}$ is hydrogen, $C_1$-$C_{18}$alkyl, $C_5$-$C_{10}$cycloalkyl, $C_2$-$C_{12}$alkenyl, phenyl-$C_1$-$C_4$alkyl or phenyl.

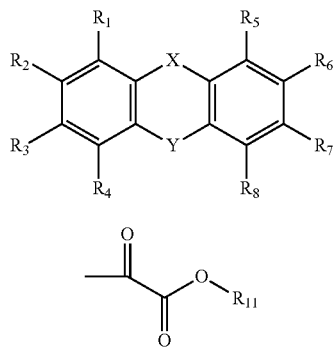

17 Claims, 1 Drawing Sheet

(51) Int. Cl.
| | |
|---|---|
| C08F 2/54 | (2006.01) |
| C09D 7/63 | (2018.01) |
| C07D 319/24 | (2006.01) |
| C07D 327/08 | (2006.01) |
| C07D 309/32 | (2006.01) |
| C07D 339/08 | (2006.01) |
| C08F 20/18 | (2006.01) |
| C08K 5/101 | (2006.01) |
| C08K 5/1535 | (2006.01) |
| C08K 5/1545 | (2006.01) |
| C08K 5/159 | (2006.01) |
| C08K 5/46 | (2006.01) |
| C09D 4/00 | (2006.01) |

(52) U.S. Cl.
CPC ......... *C07D 319/24* (2013.01); *C07D 327/08* (2013.01); *C07D 339/08* (2013.01); *C08F 2/54* (2013.01); *C08F 20/18* (2013.01); *C08K 5/101* (2013.01); *C08K 5/159* (2013.01); *C08K 5/1535* (2013.01); *C08K 5/1545* (2013.01); *C08K 5/46* (2013.01); *C09D 4/00* (2013.01); *C09D 7/63* (2018.01)

(58) Field of Classification Search
CPC .......... C08F 20/18; C08F 2/54; C07D 309/32; C07D 307/91; C07D 339/08; C07D 327/08; C07D 319/24; C09D 4/00; C09D 7/63
See application file for complete search history.

(56) References Cited

U.S. PATENT DOCUMENTS

| | | |
|---|---|---|
| 4,575,330 A | 3/1986 | Hull |
| 5,013,768 A | 5/1991 | Kiriyama et al. |
| 5,376,459 A | 12/1994 | Christner et al. |

FOREIGN PATENT DOCUMENTS

| | | |
|---|---|---|
| DE | 2261745 A1 | 6/1974 |
| DE | 2304763 A1 | 8/1974 |
| DE | 4228514 A1 | 3/1994 |
| DE | 19700064 A1 | 7/1997 |
| EP | 12339 A1 | 6/1980 |
| EP | 41125 A1 | 12/1981 |
| EP | 0126541 A1 | 11/1984 |
| EP | 245639 A1 | 9/1989 |
| EP | 339841 A3 | 4/1990 |
| EP | 438123 A3 | 11/1991 |
| EP | 445624 A3 | 2/1992 |
| EP | 0636669 A3 | 7/1995 |
| EP | 678534 A1 | 10/1995 |
| EP | 0270252 A2 | 6/1999 |
| GB | 2180358 A | 3/1987 |
| JP | S49-102677 A | 9/1974 |
| JP | 63-159379 A1 | 7/1988 |
| JP | 63-179849 A | 7/1988 |
| JP | H06-68309 A | 3/1994 |
| JP | H10-287450 A | 10/1998 |
| JP | 2016-534023 A | 11/2016 |
| WO | 90/01512 A1 | 2/1990 |
| WO | 2003/064061 A1 | 8/2003 |
| WO | 2004/074328 A1 | 9/2004 |
| WO | 2004/111044 A1 | 12/2004 |
| WO | 06/008251 A1 | 1/2006 |
| WO | 2006/120212 A1 | 11/2006 |
| WO | 2011/069947 A1 | 6/2011 |
| WO | 2015/042397 A1 | 3/2015 |
| WO | 2016/034963 A1 | 3/2016 |

OTHER PUBLICATIONS

Miyoshi H et al: "Topographical characterization of the ubiquinone reduction site of glucose dehydrogenase in *Escherichia coli* using depth-dependent fluorescent inhibitors",vol. 1412, No. 1, May 26, 1999 (May 26, 1999), pp. 29-36.
Inke Siewert et al: 11A Dinuclear Iron Complex Based on Parallel Malonate Binding Sites: Cooperative Activation of Dioxygen and Biomimetic Ligand Oxidation, vol. 14, No. 30, Oct. 20, 2008 (Oct. 20, 2008), pp. 9377-9388.
Shoji Shibata et al., "Renewed studies on the structure of didymic acid", Chemical and Pharmaceutical Bulletin, vol. 32. No. 1, Jan. 1, 1984 (Jan. 1, 1984), pp. 366-368.
William Bradley et al., "321 The selective absorption of optical antipodes by proteins. Part III", Journal of the Chemical Society, Jan. 1, 1956 (Jan. 1, 1956), p. 1622.
Bertsch at al., "Study of the spatial resolution of a new 3D microfabrication process: the microstereophotolithography using a dynamic mask-generator technique", Journal of Photochemistry and Photobiology A: Chemistry 107 (1997) 275-281.
Bocknack, et al., "Chiral b-diketonate ligands of 'pseudo planar chiral' topology: enantioselective synthesis and transition metal complexation", Tetrahedron 61 (2005) 6266-6275.
Wittig, "Radiation curing of powder coating", vol. 184, Np. 4343, Feb. 9, 1994.
Coic, et al., "Meso Heterocyclic .Analogues of 9,10-Dihydroanthraccne. XIII, On the Structure of the Products of Diacelylalion of Phenoxathiin: A Correction (1)", Aug. 1978, pp. 769-772.
Ryosuke Matsubara et al: "A Concise Synthesis of Asym metrically 4,5- Disu bstituted 9,9- Di methyl-9H-xanthenes", Synthesis, vol. 47, No. 02, Nov. 10, 2014 (Nov. 10, 2014), pp. 187-192, Abstract.
Siewert, et al., "A Dinuclear Iron Complex Based on Parallel Malonate Binding Sites: Cooperative Activation of Dioxygen and Biomimetic Ligand Oxidation", Chem. Eur. J. 2008, 14, 9377-9388, Abstract.
Journal of Synthetic Organic Chemistry, 2014.
Mieck, "Flachs versus Glas", vol. 33, pp. 366-370, 1995.
Schut, "Is dry paint in your future", Plastics World, vol. 54, No. 7, pp. 48-52, Jul. 1996.
Grunewald, "Verarbeitung glasfaserverstarkter Kunststoffe", Springer Verlag, pp. 506-615, 1967.
Office action for Japanese Patent Application No. 2019-510314, dated Jul. 30, 2019.

* cited by examiner

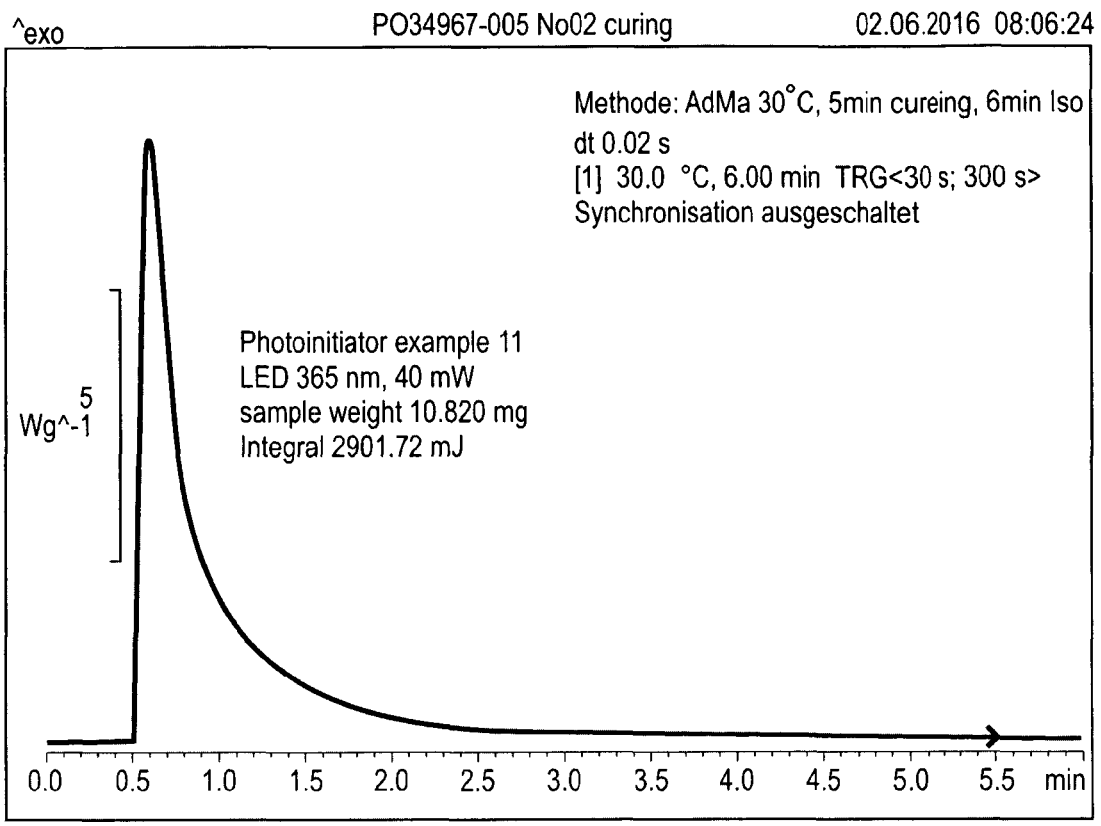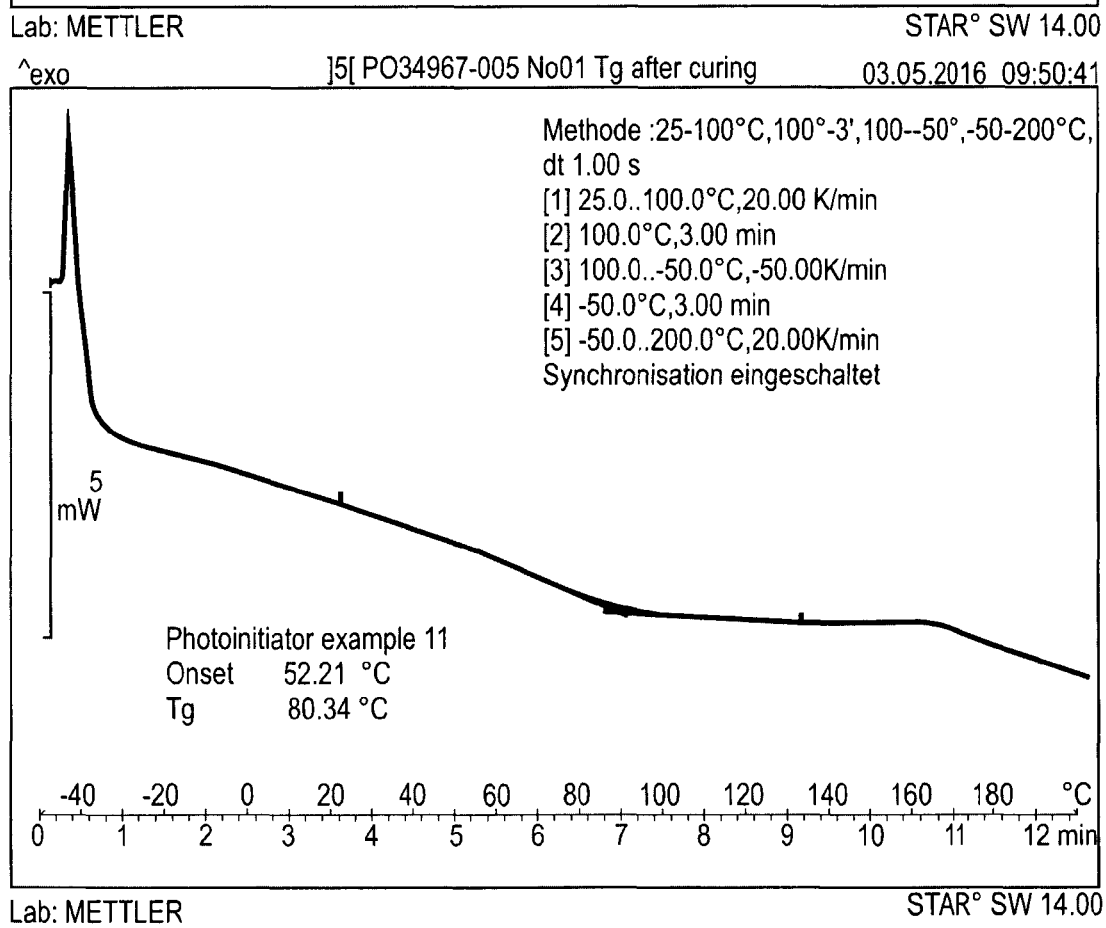

POLYCYCLIC GLYOXYLATES AS PHOTOINITIATORS

Object of the present invention are novel polycyclic photoinitiators and their use for polymerization (curing) of radically polymerizable compositions triggered by electromagnetic radiation.

We have now discovered that polycyclic glyoxylates represent highly efficient novel photoinitiators with low volatility and out-standing curing properties. The photoinitiators of the present invention can induce curing of radically polymerizable compositions upon irradiation from a variety of radiation sources. However, one special advantage of the photoinitiators according to the present invention is that good curing properties can be achieved even when providing electromagnetic radiation by means of light emitting diodes (LED).

Surprisingly, photoinitiators in which one or several glyoxylate functional groups are attached to a polycyclic aromatic or heteroaromatic system are the subject of the present invention.

BRIEF DESCRIPTION OF THE DRAWINGS

FIG. 1 illustrates the polymerization heat and the glass transition temperature of the resultant polymer when photoinitiators of Example 11 were tested at 1.5 wt.% in an acrylate-based photopolymer for 3D printing consisting of two urethane acrylates and one monofunctional monomer, as determined by means of photo-DSC and DSC (TGA/DSC 1, Mettler Toledo) after irradiation with a 365 nm LED (40 mW), These are photoinitiator compounds of the formula (1),

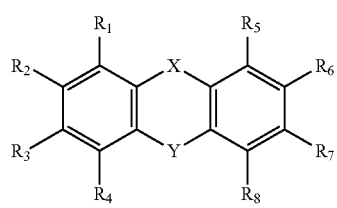

(1)

wherein
X is O, S or a direct bond;
Y is O, S or $CR_9R_{10}$;
$R_1$, $R_2$, $R_3$, $R_4$, $R_5$, $R_6$, $R_7$ and $R_8$ independently of each other are hydrogen, halogen, $C_1$-$C_{18}$alkyl, $C_5$-$C_{10}$cycloalkyl, $C_2$-$C_{18}$alkenyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (2)

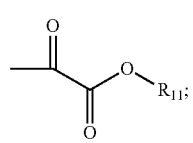

(2)

provided that one or more than one of $R_1$, $R_2$, $R_3$, $R_4$, $R_5$, $R_6$, $R_7$ or $R_8$ is a group of formula (2);

$R_9$, $R_{10}$ independently are hydrogen, $C_1$-$C_{18}$alkyl, $C_2$-$C_{12}$alkenyl, $C_5$-$C_{10}$cycloalkyl, phenyl-$C_1$-$C_4$alkyl, phenyl or together with the C atom to which they are attached form a 5-membered, 6-membered or 7-membered ring; and
$R_{11}$ is hydrogen, $C_1$-$C_{18}$alkyl, $C_5$-$C_{10}$cycloalkyl, $C_2$-$C_{12}$alkenyl, phenyl-$C_1$-$C_4$alkyl or phenyl.

In some embodiments of the present invention, the following compounds are excluded:

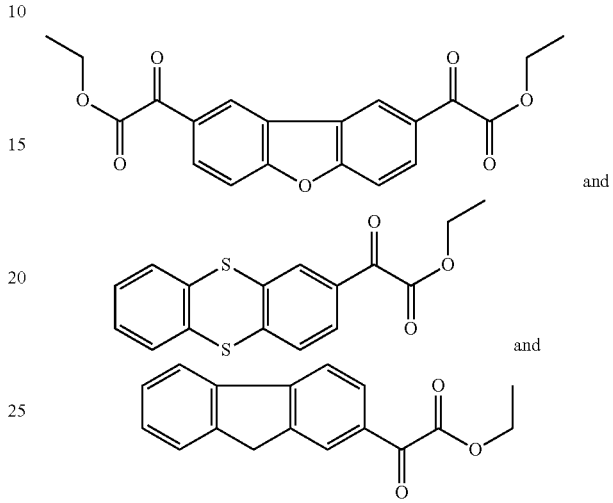

Interesting are compounds of the formula (1), wherein
(i) one of $R_1$, $R_2$, $R_3$, $R_4$, $R_5$, $R_6$, $R_7$ or $R_8$ is a group of formula (2);
or
(ii) one of $R_1$, $R_2$, $R_3$ or $R_4$ is a group of formula (2) and one of $R_5$, $R_6$, $R_7$ or $R_8$ is a group of formula (2);
$R_6$, $R_{10}$, $R_{11}$ are as defined above.

In particular interesting are compounds of the formula (1), wherein
(i) one of $R_1$, $R_2$, $R_3$, $R_4$, $R_5$, $R_6$, $R_7$ or $R_8$ is a group of formula (2);
or
(ii) one of $R_1$, $R_2$, $R_3$ or $R_4$ is a group of formula (2) and one of $R_5$, $R_6$, $R_7$ or $R_8$ is a group of formula (2);
$R_9$, $R_{10}$ independently are hydrogen, $C_1$-$C_{18}$alkyl or together with the C atom to which they are attached form a 5-membered, 6-membered or 7-membered ring;
$R_{11}$ is $C_1$-$C_{18}$alkyl.

In particular preferred are compounds of the formula (1), wherein
(i) one of $R_1$, $R_2$, $R_3$, $R_4$, $R_5$, $R_6$, $R_7$ or $R_8$ is a group of formula (2);
or
(ii) one of $R_1$, $R_2$, $R_3$ or $R_4$ is a group of formula (2) and one of $R_5$, $R_6$, $R_7$ or $R_8$ is a group of formula (2);
$R_9$, $R_{10}$ independently are hydrogen or methyl;
$R_{11}$ is methyl or ethyl.

Further emphasis is laid on compounds of the formula (1) as described above, wherein the remaining groups $R_1$ to $R_4$ and $R_5$ to $R_8$ are independently hydrogen, halogen, $C_1$-$C_4$alkyl, $C_1$-$C_4$alkoxy, $C_1$-$C_4$alkylthio, N-morpholinyl or N-piperidinyl.

In particular the remaining groups $R_1$ to $R_4$ and $R_5$ to $R_8$ are hydrogen.

$C_1$-$C_{18}$alkyl is linear or branched and is, for example $C_1$-$C_6$- or $C_1$-$C_4$alkyl. Examples are methyl, ethyl, propyl, isopropyl, 1-methylpropyl, n-butyl, sec-butyl, isobutyl, tert-butyl, pentyl, 2,2-dimethylpropyl, hexyl, heptyl, 2,4,4-trimethylpentyl, 2-ethylhexyl or n-octyl. $C_1$-$C_4$alkyl has the same meanings as given above up to the corresponding number of C-atoms.

$C_5$-$C_7$cycloalkyl is for example cyclopropyl, cyclopentyl, cyclohexyl, cycloheptyl or tricycle[3.3.1.1$^{3,7}$]dec-2-yl, especially cyclopentyl and cyclohexyl, preferably cyclohexyl. $C_1$-$C_4$alkoxy is linear or branched and is for example methoxy, ethoxy, propoxy, isopropoxy, n-butyloxy, sec-butyloxy, iso-butyloxy or tert-butyloxy, especially methoxy.

$C_5$-$C_7$cycloalkoxy is $C_5$-$C_7$cycloalkyl-O—, wherein the $C_5$-$C_7$cycloalkyl is defined as given above.

$C_2$-$C_{18}$alkenyl radicals are mono or polyunsaturated, linear or branched and are for example $C_2$-$C_8$-, $C_2$-$C_6$- or $C_2$-$C_4$alkenyl. Examples are allyl, methallyl, vinyl, 1,1-dimethyl-allyl, 2-propen-1-yl, 1-butenyl, 3-butenyl, 2-butenyl, 1,3-pentadienyl, 5-hexenyl, 1-ethenylhexyl or 7-octenyl, especially allyl or vinyl.

$C_1$-$C_4$alkylthio is linear or branched and is for example methylthio, ethylthio, propylthio, isopropylthio, n-butylthio, sec-butylthio, iso-butylthio or tert-butylthio, preferably methylthio.

The $C_1$-$C_4$alkyl and the $C_5$-$C_7$cycloalkyl in the terms di($C_1$-$C_4$alkyl)amino, $C_5$-$C_7$cycloalkylthio, and di($C_5$-$C_7$cycloalkyl)amino have the meanings as given above.

Halogen is fluorine, chlorine, bromine and iodine, especially fluorine, chlorine and bromine, preferably fluorine and chlorine.

If $R_9$ and $R_{10}$ together with the C atom to which they are attached form a 5-membered, 6-membered or 7-membered ring, preferably a saturated ring, structures like e.g.

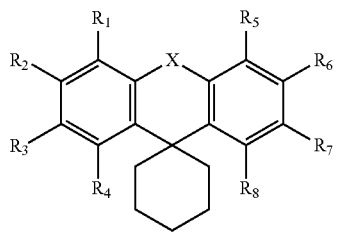

are formed.

In a specific embodiment the compound is of formula (3)

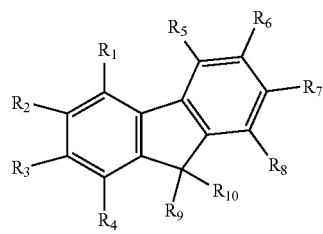

(3)

$R_1$, $R_2$, $R_3$, $R_4$, $R_5$, $R_6$, $R_7$ and $R_8$ independently of each other are hydrogen, halogen, $C_1$-$C_{18}$alkyl, $C_5$-$C_{10}$cycloalkyl, $C_2$-$C_{18}$alkenyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (2);

provided that one or more than one of $R_1$, $R_2$, $R_3$, $R_4$, $R_5$, $R_6$, $R_7$ or $R_8$ is a group of formula (2);

$R_9$, $R_{10}$ independently are hydrogen, $C_1$-$C_{18}$alkyl, $C_2$-$C_{12}$alkenyl, $C_5$-$C_{10}$cycloalkyl, phenyl-$C_1$-$C_4$alkyl, phenyl or together with the C atom to which they are attached form a 5-membered, 6-membered or 7-membered ring; and $R_{11}$ is hydrogen, $C_1$-$C_{18}$alkyl, $C_5$-$C_{10}$cycloalkyl, $C_2$-$C_{12}$alkenyl, phenyl-$C_1$-$C_4$alkyl or phenyl.

More preferred are compounds of formula (3), wherein $R_1$, $R_2$, $R_3$, $R_4$, $R_5$, $R_6$, $R_7$ and $R_8$ independently of each other are hydrogen, halogen, $C_1$-$C_{18}$alkyl, $C_2$-$C_{18}$alkenyl, phenyl, or a group of formula (2);

provided that one or more than one of $R_1$, $R_2$, $R_3$, $R_4$, $R_5$, $R_6$, $R_7$ or $R_8$ is a group of formula (2);

$R_9$, $R_{10}$ independently are hydrogen, $C_1$-$C_{18}$alkyl or together with the C atom to which they are attached form a 5-membered, 6-membered or 7-membered ring; and $R_{11}$ is $C_1$-$C_{18}$alkyl or $C_2$-$C_{12}$alkenyl.

Preferred are also compounds of formula (3), wherein $R_1$, $R_2$, $R_3$, $R_4$, $R_5$, $R_6$, $R_7$ and $R_8$ independently of each other are hydrogen or a group of formula (2);

provided that one or more than one of $R_1$, $R_2$, $R_3$, $R_4$, $R_5$, $R_6$, $R_7$ or $R_8$ is a group of formula (2);

$R_9$, $R_{10}$ independently are hydrogen or $C_1$-$C_{18}$alkyl; and $R_{11}$ is $C_1$-$C_{18}$alkyl.

In particular preferred are also compounds of formula (3), wherein $R_1$, $R_2$, $R_3$, $R_4$, $R_5$, $R_6$, $R_7$ and $R_8$ independently of each other are hydrogen or a group of formula (2);

provided that one or more than one of $R_1$, $R_2$, $R_3$, $R_4$, $R_5$, $R_6$, $R_7$ or $R_8$ is a group of formula (2);

$R_9$, $R_{10}$ independently are hydrogen or methyl; and $R_{11}$ is methyl or ethyl.

The present invention also relates to a compound of formula (1)

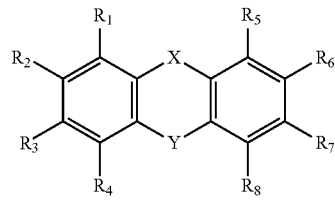

(1)

wherein

X is O, S or a direct bond;

Y is O, S or $CR_9R_{10}$;

$R_1$, $R_2$, $R_3$, $R_4$, $R_5$, $R_6$, $R_7$ and $R_8$ independently of each other are hydrogen, halogen, $C_1$-$C_4$alkyl, $C_5$-$C_7$cycloalkyl, $C_2$-$C_{18}$alkenyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (2);

provided that one or more than one of $R_1$, $R_2$, $R_3$, $R_4$, $R_5$, $R_6$, $R_7$ or $R_8$ is a group of formula (2);

$R_9$, $R_{10}$ independently are hydrogen, $C_1$-$C_{18}$alkyl, $C_2$-$C_{12}$alkenyl, $C_5$-$C_{10}$cycloalkyl, phenyl-$C_1$-$C_4$alkyl, phenyl or together with the C atom to which they are attached form a 5-membered, 6-membered or 7-membered ring; and $R_{11}$ is hydrogen, $C_1$-$C_{18}$alkyl, $C_5$-$C_{10}$cycloalkyl, $C_2$-$C_{12}$alkenyl, phenyl-$C_1$-$C_4$alkyl or phenyl;

provided that

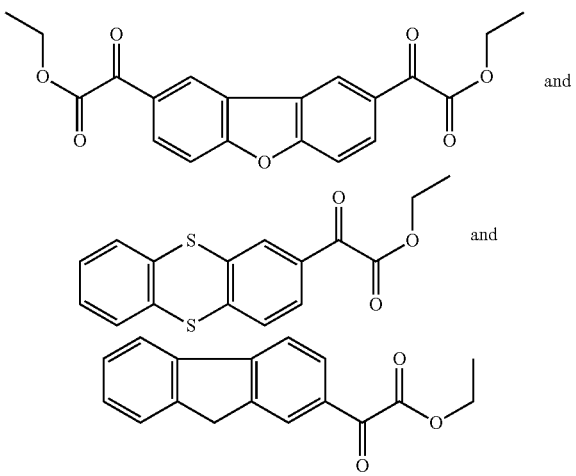

are excluded.

The terms "and/or" or "or/and" in the present context are meant to express that not only one of the defined alternatives (substituents) may be present, but also several of the defined alternatives (substituents) together, namely mixtures of different alternatives (substituents).

The term "optionally substituted" means, that the radical to which it refers is either unsubstituted or substituted.

The term "at least" is meant to define one or more than one, for example one or two or three, preferably one or two.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compositions, use, process claims as well.

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The compounds of the present invention can be made by methods well established for the synthesis of aryl glyoxylates.

One, non-limiting possibility consists of Friedel-Crafts acylation of a polycyclic compound with a suitable oxoacetate derivative (e.g. chlorooxoacetates or oxalates) to afford the corresponding mono-, di- or poly-glyoxylated polycyclic compound. Friedel-Crafts acylations on the polycyclic aromatic systems which are pertinent to the present invention are well known. These glyoxylations through Friedel-Crafts acylation reactions can be regioselective or can afford mixtures of regioisomers. For examples, glyoxylation of dibenzofurane proceeds regioselectively to afford the 2-glyoxylate- or 2,8-diglyoxylate derivatives (see Bocknack, B. M. et al, Tetrahedron (2005), 61(26), 6266-6575).

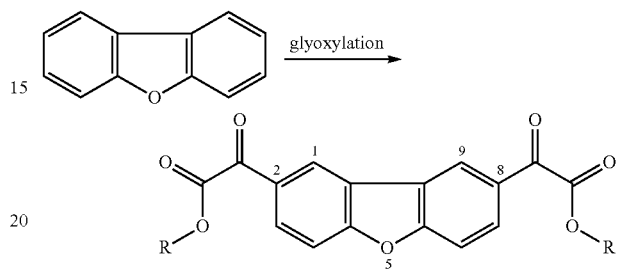

Regioselective glyoxylation is reported to occur also with thianthrene to afford the 2-glyoxylate derivative (see Kura, H. et al, PCT Int. Appl., 2000052530, 8 Sep. 2000).

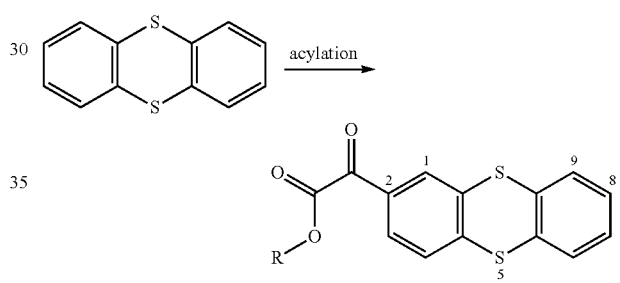

On the other hand, a mixture of 2- and 3-monoacyl- or 2,7- and 2,8-diacyl derivatives is obtained upon Friedel-Craft acylation of phenoxathiin (see e.g. Coic, J. P. et al., Journal of Heterocyclic Chemistry (1978), 15(5), 769-72).

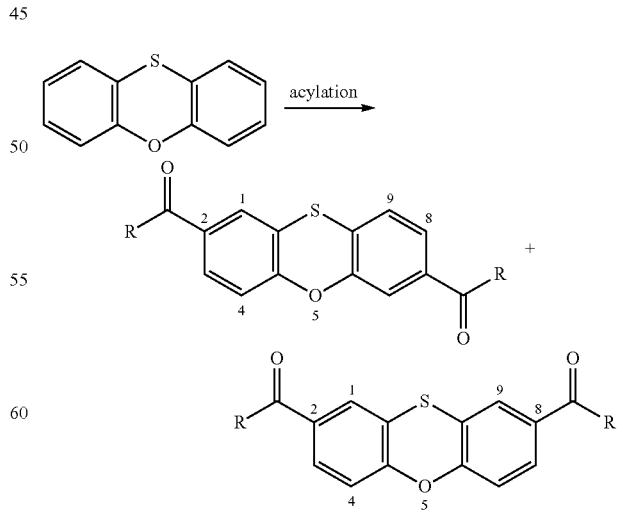

Thus, the outcome of the glyoxylations through Friedel-Crafts acylation in the other cases pertinent to this invention may be a single regioisomer or a mixture of 2 or even more regioisomers. Accordingly, subject of the invention are the single regioisomers as well as the mixture of isomers.

The present invention also relates to new photoinitiator compounds. Accordingly, subject of the invention also is a process for the preparation of a compound of the formula (1) according to the present invention by Friedel-Crafts acylation of a polycyclic aryl compound

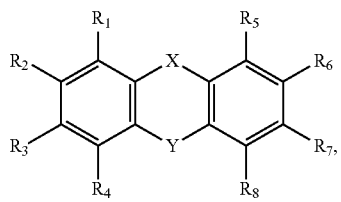
(1a)

wherein
$R_1$, $R_2$, $R_3$, $R_4$, $R_5$, $R_6$, $R_7$ and $R_8$ independently of each other are hydrogen, halogen, $C_1$-$C_4$alkyl, $C_5$-$C_7$cycloalkyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)-amino, N-morpholinyl, N-piperidinyl,
provided that at least one of $R_1$, $R_2$, $R_3$, $R_4$, $R_5$, $R_6$, $R_7$ and $R_8$ is hydrogen; and
X and Y are as defined above;
with a halogenide compound (2a) or an oxalate compound (4a) or an anhydride compound (5a)

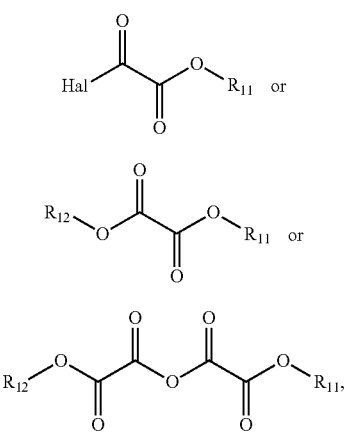

wherein
$R_{11}$ and $R_{12}$ independently of each other are hydrogen, $C_1$-$C_{18}$alkyl, $C_5$-$C_{10}$cycloalkyl, $C_2$-$C_{12}$alkenyl, phenyl-$C_1$-$C_4$alkyl or phenyl; and
Hal is a halogenide, preferably chloride;
to give the corresponding glyoxylate compound of the formula (1) according to the present invention.

In accordance with the invention, the compounds of the formula (1) can be used as photoinitiators for the photopolymerization of ethylenically unsaturated compounds. The invention therefore also relates to photopolymerizable compositions comprising (A) at least one ethylenically unsaturated photopolymerizable compound and (B) at least one photoinitiator of the formula (1)

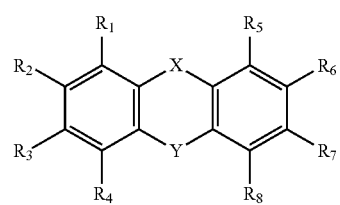
(1)

wherein
X is O, S or a direct bond;
Y is O, S or $CR_9R_{10}$;
$R_1$, $R_2$, $R_3$, $R_4$, $R_5$, $R_6$, $R_7$ and $R_8$ independently of each other are hydrogen, halogen, $C_1$-$C_{18}$alkyl, $C_5$-$C_{10}$cycloalkyl, $C_2$-$C_{18}$alkenyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (2)

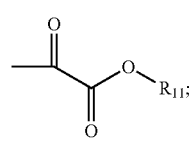
(2)

provided that one or more than one of $R_1$, $R_2$, $R_3$, $R_4$, $R_5$, $R_6$, $R_7$ or $R_8$ is a group of formula (2);
$R_9$, $R_{10}$ independently are hydrogen, $C_1$-$C_{18}$alkyl, $C_2$-$C_{12}$alkenyl, $C_5$-$C_{10}$cycloalkyl, phenyl-$C_1$-$C_4$alkyl, phenyl or together with the C atom to which they are attached form a 5-membered, 6-membered or 7-membered ring; and
$R_{11}$ is hydrogen, $C_1$-$C_{18}$alkyl, $C_5$-$C_{10}$cycloalkyl, $C_2$-$C_{12}$alkenyl, phenyl-$C_1$-$C_4$alkyl or phenyl.

The composition may comprise additionally to the component (B), (x) at least one further photoinitiator (C), and/or (xi) further coinitiators (D) and/or (xii) other additives (E).

The unsaturated compounds may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Interesting also are resins which are modified with silicon or fluor, e.g. silicon acrylates. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, acrylated polyesters, polyesters containing vinyl ether or epoxy groups, and also acrylated polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl) propane, and also novolaks and resols. Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (A) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis (methacrylamidopropoxy) ethane, β-methacrylamidoethyl methacrylate and N[(β-hydroxyethoxy)-ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth)acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. It is preferred to use mixtures of polyol (meth)acrylates.

Binders as well can be added to these novel compositions, and this is particularly expedient when the photopolymerizable compounds are liquid or viscous substances. The quantity of binder may, for example, be 5-95%, preferably 10-90% and especially 40-90%, by weight relative to the overall solids content. The choice of binder is made depending on the field of application and on properties required for this field, such as the capacity for development in aqueous and organic solvent systems, adhesion to substrates and sensitivity to oxygen.

Examples of binders with high molecular weight (oligomeric) polyunsaturated compounds are acrylate epoxy resins, acrylate or vinyl-ether- or epoxy-group-containing polyesters, polyurethanes and polyethers.

Examples of suitable binders are polymers having a molecular weight of about 1000 to 2000000, preferably 10000 to 1000000. Examples are: homo- and copolymers of acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethylenedipamide), and polyesters such as poly(ethylene glycol terephtalate) and poly(hexamethylene glycol succinate) and polyimides.

Suitable binders can also be a powder.

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heatcurable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are crosslinked by means of thermal aftertreatment. The binder can simultaneously bear the radically photopolymerizable and the chemically or thermally curable function, providing a so-called dual-cure binder.

In addition to the photoinitiator the photopolymerizable mixtures may include various additives (E). Examples of these are thermal inhibitors, which are intended to prevent premature polymerization, examples being hydroquinone, hydroquinine derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilizers are disclosed in WO 04/074328, 10 page 12, line 9 to page 14, line 23, said disclosure hereby is incorporated by reference. Further additives known in the art may be added, as for example antistatics, flow improvers and adhesion promoters.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309.

It is further possible to add chain transfer agents which are customary in the art to the compositions according to the invention. Examples are mercaptanes, amines and benzothiazol.

Photopolymerization can also be accelerated by adding further photosentisizers which shift or broaden the spectral sensitivity. These are, in particular, aromatic carbonyl compounds, for example benzophenone, thioxanthone, anthraquinone and 3-acylcoumarin derivatives, and also 3-(aroylmethylene)thiazolines, camphor quinone, but also eosine, rhodamine and erythrosine dyes, as well as all compounds which can be used as coinitiators as described above.

Examples of suitable sensitizer compounds (D) are disclosed in WO 06/008251, page 36, line 30 to page 38, line 8, the disclosure of which is hereby incorporated by reference.

In some embodiments, the present invention relates to the use of the following compounds:

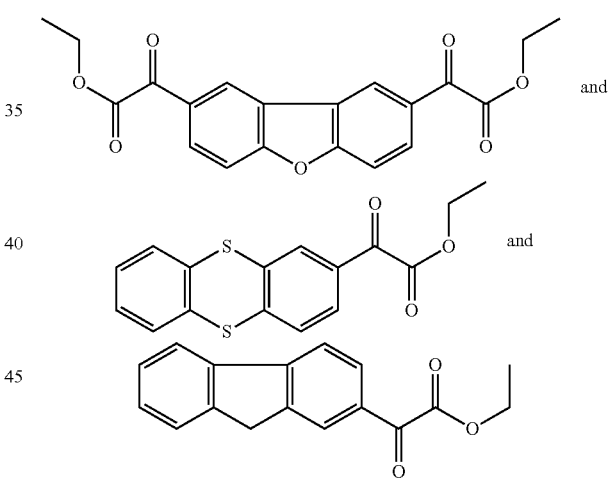

as photoinitiators.

The curing process can be assisted by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (E) a photoreducable dye, e.g., xanthene-, benzoxanthene-, benzothioxanthene-, thiazine-, pyronine-, porphyrine- or acridine dyes, and/or trihalogenmethyl compounds which can be cleaved by irradiation. Similar compositions are for example described in EP 445624. Further customary additives, depending on the intended use, are optical brighteners, fillers, pigments, dyes, wetting agents or levelling assistants.

In order to cure thick and pigmented coatings it is appropriate to add glass microspheres or pulverized glass fibres, as described for example in U.S. Pat. No. 5,013,768.

The compositions may also comprise dyes and/or white and colored pigments. Depending on the kind of application organic as well as anorganic pigments are used. Such additives are known to the person skilled in the art, some examples are titan dioxide pigments, e.g. of the rutile type or anatas type, carbon black Russ, zinc oxide, such as zink white, iron oxide, such as iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bisazo pigments, as well as metal complexes thereof, phthalocyanine pigments, polycyclic pigments, such as perylene-, anthraquinone-, thioindigo-, chinacridone- or triphenylmethane pigments, as well as diketopyrrolo-pyrole-, isoindolinone-, e.g. tetrachlorisoindolinone-, isoindoline-, dioxazin-, benzimidazolone- and chinophthalone pigments.

The pigments are employed alone or in combination in the compositions according to the invention.

Depending on the intended use the pigments are used in amount customary in the art, for example in an amount of 1-60% by weight, or 10-30% by weight, based on the whole formulation.

The compositions may also comprise organic dyes of different classes. Examples are azo dyes, methin dyes, anthraquinone dyes or metal complex dyes. Customary concentrations are for example 0.1-20%, in particular 1-5%, based on the whole formulation.

The choice of additive is made depending on the field of application and on properties required for this field. The additives described above are customary in the art and accordingly are added in amounts which are usual in the respective application.

The invention also provides compositions comprising as component (A) at least one ethylenically unsaturated photopolymerizable compound which contains some solvent, is emulsified, dispersed or dissolved in water. Many variants of such radiation-curable aqueous prepolymer dispersions are commercially available.

A prepolymer dispersion is understood as being a dispersion of water and at least one prepolymer dispersed therein. The amount of radiation curable prepolymer or prepolymer mixture, dispersed in the water for example ranges from 20 to 95% by weight, in particular from 30 to 70% by weight. In these compositions the sum of the percentages given for water and prepolymer is in each case 100, with auxiliaries and additives (e.g. emulsifiers) being added in varying quantities depending on the intended use.

The radiation-curable aqueous prepolymer dispersions are known polymeric systems, comprising mono- or polyfunctional ethylenically unsaturated prepolymers, that have an average molecular weight Mn (in g/mol) of at least 400, in particular from 500 to 100'000. Prepolymers with higher molecular weights, however, may also be considered depending on the intended application. Use is made, for example, of polyesters having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight Mn (in g/mol) of at least 600, additionally comprising polymerizable C—C double bonds. Other suitable aqueous dispersions, based on specific alkyl (meth)acrylate polymers, are described in EP 41125.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the novel photoinitiators. It is of course also possible to use mixtures with known photoinitiators (C), for example mixtures with camphor quinone; benzophenone, benzophenone derivatives, such as 2,4,6-trimethylbenzophenone, 2-methylbenzophenone, 3-methyl-benzophenone, 4-methylbenzophenone, 2-methoxycarbonylbenzophenone 4,4'-bis-(chloromethyl)benzophenone, 4-chlorobenzophenone, 4-phenylbenzophenone, 3,3'-dimethyl-4-methoxybenzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino) benzophenone, 4,4'-bis(diethylamino)benzophenone,

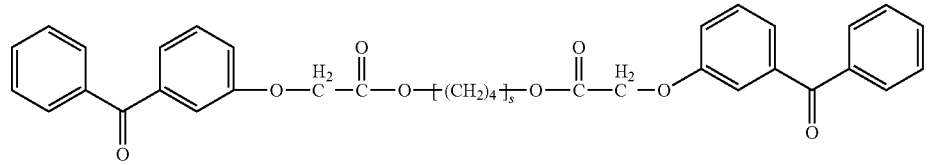

with s=1-20, a mixture of

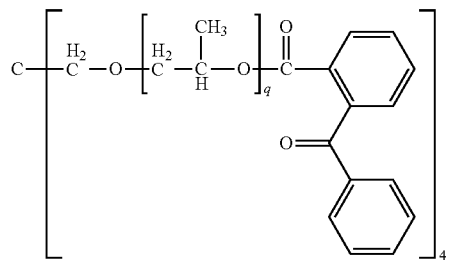

with q=about 2 and

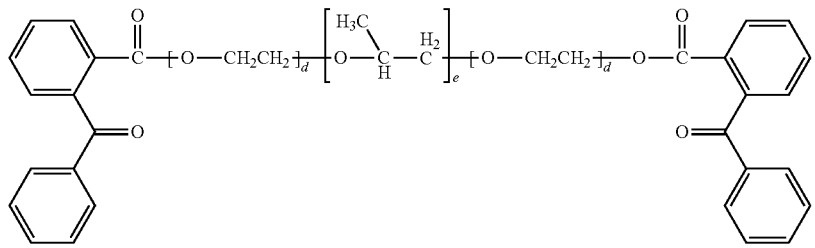

wherein the sum of d and e is about 14, where d is greater than e,

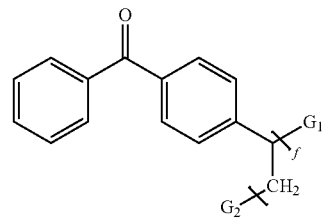

with f=about 14;

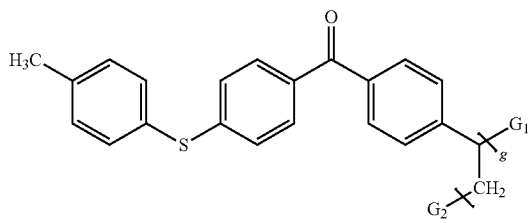

with g=about 12;

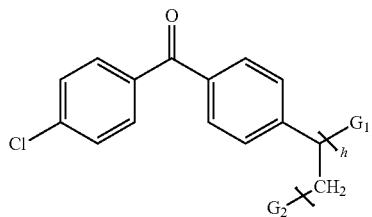

with h=about 13, and any blends or admixtures of the above mentioned compounds; thioxanthones, thioxanthone derivatives, polymeric thioxanthones as for example OMNIPOL TX; ketal compounds, as for example benzildimethylketal; acetophenone, acetophenone derivatives, for example a-hydroxycycloalkyl phenyl ketones or a-hydroxyalkyl phenyl ketones, such as for example 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropyl-benzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]-phenyl}-2-methyl-propan-1-one; 2-hydroxy-1-{4-[4-(2-hydroxy-2-methyl-propionyl)-phenoxy]-phenyl}-2-methyl-propan-1-one; dial koxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl)aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl α-oxo benzeneacetate, oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenylacetoxy)-propoxy]-ethyl ester; ketosulfones, e.g. ESACURE KIP 1001 M; oximeesters, e.g. 1,2-octanedione 1-[4-(phenylthio)phenyl]-2-(O-benzoyloxime), ethanone 1-[9-ethyl-6-(2-methylbenzoyl)-9H-carbazol-3-yl]-1-(O-acetyloxime), 9H-thioxanthene-2-carboxaldehyde 9-oxo-2-(O-acetyloxime), peresters, e.g. benzophenone tetracarboxylic peresters as described for example in EP 126541, monoacyl phosphine oxides, e.g. (2,4,6-trimethyl-benzoyl)diphenylphosphine oxide, ethyl (2,4,6 trimethyl-benzoyl phenyl) phosphinic acid ester; bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide, bis-(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl[1,3,5]triazine, 2-(4-methoxy-phenyl)-4,6-bis-trichloromethyl[1,3,5]triazine, 2-(3,4-di methoxy-phenyl)-4,6-bis-trichloromethyl-[1,3,5]triazine, 2-methyl-4,6-bis-trichloromethyl[1,3,5]triazine, hexaarylbisimidazole/coinitiators systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrryl-phenyl)titanium. Further, borate compounds can be used as coinitiators. As additional photoinitiators oligomeric compounds such as for example oligomeric alpha hydroxyl ketones e.g. 2-hydroxy-1-{1-[4-(2-hydroxy-2-methyl-propionyl)-phenyl]-1,3,3-trimethyl-indan-5-yl}-2-methyl-propan-1-one, ESACURE KIP, or oligomeric alpha amino ketones may be employed as well.

Where the novel photoinitiator systems are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17-25), aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-isopropylbenzene) ($\eta^6$-cyclopentadienyl)iron (II) hexafluorophosphate or oxime sulfonates. Suitable sulfonium salts are obtainable, for example, under the trade names ° Cyracure UVI-6990, ° Cyracure UVI-6974 (Union Carbide), ° Degacure KI 85 (Degussa), SP-55, SP-150, SP-170 (Asahi Denka), GE UVE 1014 (General Electric), SarCat® KI-85 (=triarylsulfonium hexafluorophosphate; Sartomer), SarCat® CD 1010 (=mixed triarylsulfonium hexafluoroantimonate; Sartomer); SarCat® CD 1011 (=mixed triarylsulfonium hexafluorophosphate; Sartomer).

Suitable iodonium salts are e.g. tolylcumyliodonium tetrakis(pentafluorophenyl)borate, 4-[(2-hydroxy-tetradecyloxy)phenyl]phenyliodonium hexafluoroantimonate or hexafluorophosphate (SarCat® CD 1012; Sartomer), tolylcumyliodonium hexafluorophosphate, 4-isobutylphenyl-4'-methylphenyliodonium hexafluorophosphate, 4-octyloxyphenylphenyl-iodonium hexafluorophosphate or hexafluoroantimonate, bis(dodecylphenyl)iodonium hexafluoroantimonate or hexafluorophosphate, bis(4-methylphenyl)iodonium hexafluorophosphate, bis(4-methoxyphenyl)iodonium hexafluorophosphate, 4-methylphenyl-4'-ethoxyphenyliodonium hexafluorophosphate, 4-methylphenyl-4'-dodecylphenyliodonium hexafluorophosphate, 4-methylphenyl-4'-phenoxyphenyliodonium hexafluorophosphate. Of all the iodonium salts mentioned, compounds with other anions are, of course, also suitable.

Suitable examples of oximesulfonates are α-(octylsulfonyloxyimino)-4-methoxybenzylcyanide, 2-methyl-α-[5-[4-[[methyl-sulfonyl]oxy]imino]-2(5H)-thienylidene]-benzeneacetonitrile, 2-methyl-α-[5-[4-[[(n-propyl)sulfonyl]oxy]imino]-2(5H)-thienylidene]-benzeneacetonitrile, 2-methyl-α-[5-[4-[[(camphoryl)sulfonyl]oxy]imino]-2(5H)-thienylidene]-benzeneacetonitrile, 2-methyl-α-[5-[4-[[(4-methylphenyl)sulfonyl]oxy]imino]-2(5H)-thienylidene]-benzeneacetonitrile, 2-methyl-α-[5-[4-[[(n-octyl)sulfonyl]oxy]imino]-2(5H)-thienylidene]benzeneacetonitrile, 2-methyl-α-[5-[[[4-[[(4-methylphenyl)sulfonyl]oxy]phenyl]sulfonyl]oxy]imino]-2(5H)-thienylidene]-benzeneacetonitrile, 1,1'-[1,3-propanediylbis(oxy-4,1-phenylene)]bis[2,2,2-trifluoro-bis[O-(trifluoromethylsulfonyl)oxime]-ethanone, 1,1'-[1,3-propanediylbis(oxy-4,1-phenylene)]bis[2,2,2-trifluoro-bis[O-(propylsulfonyl) oxime]-ethanone, 1,1'-[1,3-propanediylbis(oxy-4,1-phenylene)]bis[2,2,2-trifluoro-bis[O-((4-methylphenyl) sulfonyl)oxime]-ethanone, 2-[2,2,3,3,4,4,5,5,6,6,7,7-dodecafluoro-1-(nonafluorobutylsulfonyloxyimino) heptyl]-fluorene, 2-[2,2,3,3,4,4,4-heptafluoro-1-(nonafluorobutylsulfonyloxyimino)-butyl]-fluorene, 2-[2,2,3,3,4,4,5,5,6,6,7,7-dodecafluoro-1-(nonafluorobutylsulfonyloxyimino)-heptyl]-9-thia-fluorene. This list is not meant to be conclusive for additional photoinitiator compounds to be used in combination with the novel compounds of the inventions.

The photopolymerizable compositions generally comprise 0.05 to 15% by weight, preferably 0.1 to 10% by weight, of the photoinitiator, based on the composition. The amount refers to the sum of all photoinitiators added, if mixtures of initiators are employed. Accordingly, the amount either refers to the photoinitiator (B) or the photoinitiators (B)+(C).

The photopolymerizable compositions can be used for various purposes, for example printing, such as intaglio printing, flexographic printing, screen printing, offset printing, gravure printing, lithography or continuous or dropwise ink-jet printing on for example material pretreated in accordance with the process as disclosed in WO 03/064061 using generally known formulations, for example in publishing, packaging or shipping, in logistics, in advertising, in security printing or in the field of office equipment, as a clear finish, as a colored finish, as a white finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as photoresists, e.g. etch resists, electroplating resists, or permanent resists, both liquid and dry films, as photostructurable dielectricum and as solder masks for electronic circuits, as resists to manufacture color filters for any type of display applications or to generate structures in the manufacturing process of plasma-display panels and electroluminescence displays, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and chips, or as coatings for optical fibres, or for producing optical lenses, e.g. contact lenses or Fresnel lenses.

The compositions according to the invention are further suitable for the production of medical equipment, auxiliaries or implants.

Further the compositions according to the invention are suitable for the preparation of gels with thermotropic properties, as for example described in DE 19700064 and EP 678534.

The compositions according to the invention can also be used in dry paint film, as for example described in Paint&Coatings Industry, April 1997, 72 or Plastics World, vol. 54, no. 7, p 48(5).

The novel photoinitiators may additionally be employed as initiators for emulsion polymerizations, pearl polymerizations or suspension polymerizations, as polymerization 25 initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions act as a crosslinking agent which renders the film insoluble. The monounsaturated monomer functions act as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel photoinitiators and photoinitiator mixtures can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutile titanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation curing of the coating with ultraviolet and/or visible light, using for example medium pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation curable powder coatings can be formulated to melt at lower temperatures without the unwanted effect of shortening their lifetime. For this reason, they are also suitable as coatings for heat-sensitive substrates, for example wood or plastics.

In addition to the novel photoinitiators, the powder coating formulations may also include UV absorbers. To appropriate examples is referred above.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or SiO2 to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating techniques, for example by printing, e.g. by intaglio printing, lithographic printing, flexographic printing, inkjet printing, screen printing, gravure printing, spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination. The quantity applied (coat thickness) and the nature of the substrate (layer support) are 10 dependent on the desired field of application. The range of coat thicknesses generally comprises values from about 0.01 µm to more than 100 µm, for example 20 mm or 0.02 to 10 cm, preferably 0.5 to 100 µm.

The compositions according to the invention are also suitable for use in UV-curing adhesives, e.g. in the preparation of pressure-sensitive adhesives, laminating adhesives, hot-melt adhesives, moisture-cure adhesives, silane reactive adhesives or silane reactive sealants and the like, and related applications.

Said adhesives can be hot melt adhesives as well waterborne or solvent borne adhesives, liquid solventless adhesives or 2-part reactive adhesives. In particular suitable are pressure-sensitive adhesives (PSA), for example UV-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers.

The novel photoinitiators further find application in formulations for negative resists, having a very high sensitivity to light and being able to be developed in an aqueous alkaline medium without swelling. They are suitable as photoresists for electronics (electroplating resist, etch resist, solder resist), the production of printing plates, such as offset printing plates or flexo printing plates, for the production of printing forms for relief printing, planographic printing, rotogravure or of screen printing forms, for the production of relief copies, for example for the production of texts in braille, for the production of stamps, for use in chemical milling or as a microresist in the production of integrated circuits. The possible layer supports, and the processing conditions of the coating substrates, are just as varied.

The compositions according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 µm to 10 µm, while for printed circuits it is from 1.0 µm to about 100 µm. Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be addressed pixel by pixel to generate digital images, as is, for example, described by A. Bertsch, J. Y. Jezequel, J. C. Andre in Journal of Photochemistry and Photobiology A: Chemistry 1997, 107, p. 275-281 and by K.-P. Nicolay in Offset Printing 1997, 6, p. 34-37.

Following the imagewise exposure of the material and prior to development, it may be advantageous to carry out thermal treatment for a short time. In this case only the exposed sections are thermally cured. The temperatures employed are generally 50-150° C., preferably 80-130° C.; the period of thermal treatment is in general between 0.25 and 10 minutes.

Conjugated polymers, like e.g. polyanilines can be converted from a semiconductive to a conductive state by means of proton doping. The oxime-sulfonates of the present invention can also be used to imagewise irradiate compositions comprising such conjugated polymers in order to form conducting structures (exposed areas) embedded in insulating material (non-exposed areas). Such materials can for example be used as wiring and connecting parts for the production of electric and electronic devices. The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation. After the exposure and, if implemented, thermal treatment, the unexposed areas of the photosensitive coating are removed with a developer in a manner known per se. As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset and flexo inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions. Another field where photocuring is employed is the coating of metals, in the case, for example, of the coating of metal plates and tubes, cans or bottle caps, and the photocuring of polymer coatings, for example of floor or wall coverings based on PVC. Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366-370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also particular interest in less intense lamps, for example of the type TL40W/03 or TL40W/05. The intensity of these lamps corresponds approximately to that of sunlight. It is also possible to use direct sunlight for curing. A further advantage is 10 that the composite composition can be removed from the light source in a partly cured, plastic state and can be shaped, with full curing taking place subsequently.

The compositions and compounds according to the invention can be used for the production of holographies, waveguides, optical switches wherein advantage is taken of 15 the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g. through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

The photopolymerizable compositions further can be used for the production of functional glass, as is for example described in JP 10 287450 A.

The photocurable compositions of the invention can further be used for curing of charged monomers, e.g. acrylates with NH4Cl-groups etc. Such compositions are for example employed for preparing polyelectrolytes or corresponding copolymers.

The invention also provides a process for the photopolymerization of monomeric, oligomeric or polymeric compounds containing at least one ethylenically unsaturated double bond, which comprises adding to the abovementioned compounds at least one photoinitiator or photoinitiator mixture as described above and irradiating the resulting composition with electromagnetic radiation, for example light of the wavelength 200 to 600 nm or with particulate radiation, such as for example electron beam or X-ray; as well as the use of a photoinitiator or photoinitiator mixture as defined above for the photopolymerization of monomeric, oligomeric or polymeric compounds containing at least one ethylenically unsaturated double bond.

Subject of the invention also is a process as described above for the preparation of pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules. The photoinitiators according to the present invention are especially suitable for 3D printing.

The invention further provides a coated substrate which is coated on at least one surface with a composition as described above. In some embodiments, the composition coated on the substrate may further be cured, i.e. may be polymerized or crosslinked.

The present invention also relates to an article comprising a polymerized or crosslinked composition obtained by curing a polymerizable composition as described above. The article according to the invention may e.g. be obtained in a three-dimensional printing process (3D printing), such as stereolithograpy.

In addition, the present invention relates to a polymerized or crosslinked composition obtained by curing the photopolymerizable composition according to the invention described above.

The sensitivity of the novel compositions to radiation generally extends from about 190 nm through the UV region and into the infrared region (about 20,000 nm, in particular 1200 nm), especially from 190 nm to 650 nm (depending on the photoinitiator moiety, optionally in combination with a sensitizer as described hereinbefore) and therefore spans a very broad range. Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, super high-, high- and low-pressure mercury lamps, possibly with metal halide dopes (metal-halogen lamps), micro-wave-stimulated metal vapour lamps, excimer lamps, superactinic fluorescent tubes, fluorescent lamps, argon incandescent lamps, electronic flashlights, photographic flood lamps, electron beams and X-rays. The distance between the lamp and the substrate to be exposed in accordance with the invention may vary depending on the intended application and the type and output of lamp, and may be, for example, from 1 cm to 150 cm. Laser light sources, for example excimer lasers, such as krypton F lasers for exposure at 248 nm are also suitable. Lasers in the visible region can also be employed.

In a preferred embodiment, the actinic radiation is provided by light emitting diodes (LED) or organic light emitting diodes (OLED), e.g. UV light emitting diodes (UV-LED). Said LEDs allow instant on and off switching of the radiation source. Further, UV-LEDs generally have a narrow wavelength distribution and offer the possibility to customize the peak wavelength and also provide an efficient conversion of electric energy to UV radiation.

As mentioned above, depending on the light source used it is advantageous in many cases to employ a sensitizer, as described above, whose absorption spectrum coincides as closely as possible to the emission spectrum of the radiation source.

The examples which follow illustrate the invention in more detail, without restricting the scope said examples only. Parts and percentages are, as in the remainder of the description and in the claims, by weight, unless stated otherwise.

A) SYNTHESIS EXAMPLES

Example 1: Ethyl 2-[7-(2-ethoxy-2-oxo-acetyl)-9H-xanthen-2-yl]-2-oxo-acetate (Compound 1)

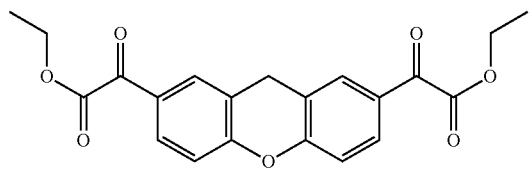 [SMILES: CCOC(=O)C(=O)c1ccc2c(c1)Cc1cc(C(=O)C(=O)OCC)ccc1O2]

Xanthene (15.03 g, 0.082 mol) was dissolved in 65 g of 1,2-dichloroethane and cooled in an ice bath. Aluminium chloride (54.40 g, 0.408 mol) was then added under stirring to form a brown solution. Within 1 hour a solution of ethyl chlorooxoacetate (48.10 g, 0.352 mol) in 28 g of 1,2-dichloroethane was charged at 5° C. The resulting mixture was stirred for 20 hours at 20° C. and was thereafter slowly poured into a stirred mixture of 254.2 g of ice, 254.8 g of water, 51.6 g of 32% hydrochloric acid and 170.0 g of 1,2-dichloroethane. The organic layer was separated, washed twice with 50 mL of water, dried over $Na_2SO_4$ and evaporated. The residue was dissolved in 40 g of ethyl acetate, washed twice with 50 mL of water, dried over $Na_2SO_4$, filtrated over a small pad of silica gel and evaporated to afford 4.2 g of compound 1 as a yellowish solid, mp. 103-109° C.

$^1$H-NMR (400 MHz, $CDCl_3$), δ[ppm]: 1.41 (t, 6H), 4.20 (s, 2H), 4.48 (q, 4H), 7.20 (d, 2H), 7.94-7.96 (m, 4H).

$^{13}$C-NMR (75.5 MHz, $CDCl_3$), δ[ppm]: 14.1, 27.14, 62.5, 117.5, 120.3, 128.3, 131.6, 134.8, 155.9, 163.8, 184.4.

UV-Vis (acetonitrile): $\lambda_{max}$=322 nm.

Example 2: Ethyl 2-(9,9-di methylxanthen-2-yl)-2-oxo-acetate (Compound 2)

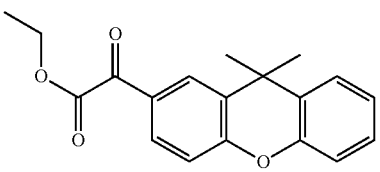 [SMILES: CCOC(=O)C(=O)c1ccc2c(c1)C(C)(C)c1ccccc1O2]

9,9-Dimethyl xanthene (4.50 g, 21 mmol) was dissolved in 37.5 g of 1,2-dichloroethane. Ethyl chlorooxoacetate (6.14 g, 45 mmol) was added at room temperature. The resulting yellow mixture was cooled to −5° C. Aluminium chloride (6.28 g, 47 mmol) was then added under stirring to form a dark red solution. After stirring for 20 hours at 23° C. an additional amount of ethyl chlorooxoacetate (0.64 g, 4.6 mmol) was added and reaction continued at room temperature. A TLC analysis after 2 hours indicated full conversion of 9,9-dimethyl xanthene. The mixture was then slowly poured into 150 g of ice under stirring. After addition of 50 mL of 1,2-dichloroethane and 150 mL of water the organic layer was separated, washed with 150 mL of water, dried over MgSO$_4$ and evaporated. Column chromatography (55 g of silica gel, eluent 1:500 mL of ethyl acetate, eluent 2: dichloromethane) afforded 0.5 g of compound 3 and 2.5 g of the desired compound 2.

$^1$H-NMR (400 MHz, CDCl$_3$), δ[ppm]: 1.46 (t, 3H), 1.72 (s, 6H), 4.48 (q, 2H), 7.08-7.11 (m, 1H), 7.14-7.18 (m, 2H), 7.23-7.28 (m, 1H), 7.45 (d, 1H), 7.89 (d, 1H), 8.21 (s, 1H).

Example 3: Ethyl 2-[7-(2-ethoxy-2-oxo-acetyl)-9,9-dimethyl-xanthen-2-yl]-2-oxo-acetate (Compound 3)

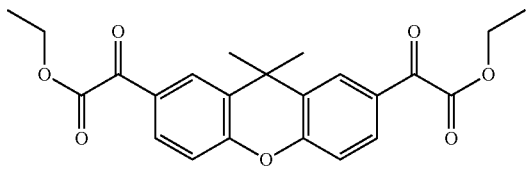 [SMILES: CCOC(=O)C(=O)c1ccc2c(c1)C(C)(C)c1cc(C(=O)C(=O)OCC)ccc1O2]

Compound 2 (2.45 g, 8 mmol) was dissolved in 32.3 g of 1,2-dichloroethane and 1 g of sulfolane. A solution of ethyl chlorooxoacetate (4.38 g, mmol) dissolved in 4.13 g of 1,2-dichloroethane was added at room temperature. The resulting greenish mixture was cooled to −3° C. Aluminium chloride (2.38 g, 18 mmol) was then added under stirring to form a dark red mixture. After stirring for 20 hours at 23° C. an additional amount of aluminium chloride (4.00 g, 30 mmol) was added and the reaction mixture stirred for 30 hours at room temperature. The mixture was then slowly poured into 150 g of ice under stirring. After addition of 30 mL of 1,2-dichloroethane and 90 mL of 32% hydrochloric acid the organic layer was separated, washed twice with 100 mL of brine, dried over MgSO$_4$ and evaporated. Column chromatography (30 g of silica gel, eluent:cyclohexane/ethyl acetate 9.5:0.5) afforded 1.0 g of the title compound as a yellowish solid.

$^1$H-NMR (400 MHz, CDCl$_3$), δ[ppm]: 1.46 (t, 6H), 1.72 (s, 6H), 4.49 (q, 4H), 7.20 (d, 2H), 7.94 (dd, 2H), 8.22 (d, 2H).

$^{13}$C-NMR (75.5 MHz, CDCl$_3$), δ[ppm]: 14.1, 32.9, 34.2, 62.4, 117.4, 128.8, 129.5, 130.3, 130.7, 154.3, 163.7, 184.6.
UV-Vis (MeOH): λ$_{max}$=319 nm.

Example 4: Ethyl 2-oxo-2-thianthren-2-yl-acetate (Compound 4)

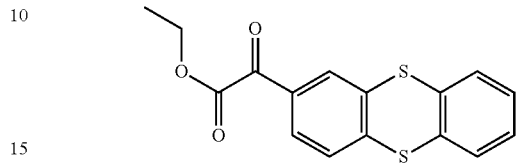

Compound 4 was prepared from thiantrene in analogy to compound 2 in 68% yield.

$^1$H-NMR (400 MHz, CDCl$_3$), δ[ppm]: 1.44 (t, 3H), 4.47 (q, 2H), 7.25-7.29 (m, 2H), 7.44-7.50 (m, 2H), 7.57 (d, 1H), 7.89 (d, 1H), 8.11 (s, 1H).

(Compound 5)

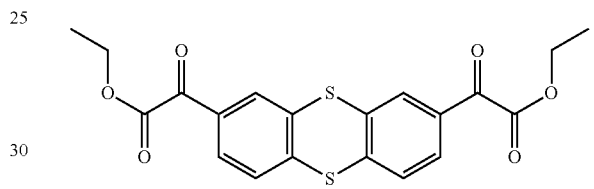

0.1 g of compound 5 in form of a yellow solid were isolated during column chromatography as a by-product, mp=123-129° C.
UV-Vis (Ethyl acetate): λ$_{max}$=288 nm and 327 nm.
$^1$H-NMR (400 MHz, CDCl$_3$), δ[ppm]: 1.45 (t, 6H), 4.47 (q, 4H), 7.60 (d, 2H), 7.95 (d, 2H), 8.11 (s, 2H).

Example 5: Ethyl 2-[8-(2-ethoxy-2-oxo-acetyl)thianthren-2-yl]-2-oxo-acetate (Compound 5)

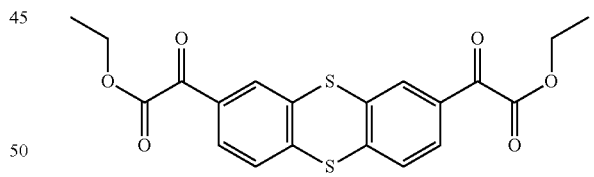

Aluminium chloride (37.00 g, 277 mmol) was added in portions into a mixture of ethyl chlorooxoacetate (34.70 g, 254 mmol) and sulfolane (0.60 g) in 100 g of 1,2-dichloroethane. A solution of thiantrene (10.00 g, 46 mmol) in 120 g of 1,2-dichloroethane was added into the red-orange mixture within 1 hour and stirred at room temperature. A TLC analysis indicated a full conversion of thiantrene after 1 hour. The reaction mixture was poured into water/ice under stirring. The organic layer was separated, washed three times with water and evaporated. After column chromatography (silica gel, eluent: cyclohexane/ethyl acetate 9:1) the crude product was obtained. A second column chromatography (silica gel, eluent: toluene/cyclohexane 1:1) was performed to isolate 0.40 g of the desired compound 5 as a yellowish solid, mp=123-129° C.

UV-Vis (Ethyl acetate): $\lambda_{max}$=288 nm and 327 nm.
$^1$H-NMR (400 MHz, CDCl$_3$), δ[ppm]: 1.45 (t, 6H), 4.47 (q, 4H), 7.60 (d, 2H), 7.95 (d, 2H), 8.11 (s, 2H).

Example 6: Ethyl 2-[8-(2-ethoxy-2-oxo-acetyl) dibenzo-p-dioxin-2-yl]-2-oxo-acetate and/or ethyl 2-[7-(2-ethoxy-2-oxo-acetyl)dibenzo-p-dioxin-2-yl]-2-oxo-acetate (Compound 6)

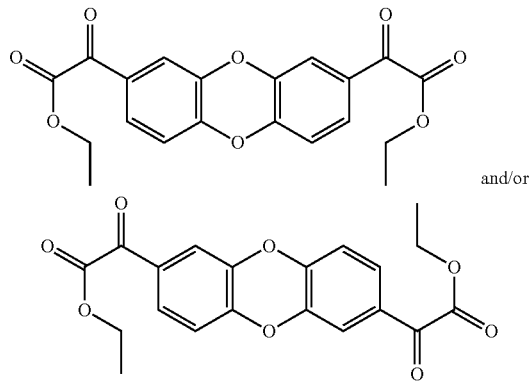

and/or

Ethyl chlorooxoacetate (74.7 g, mol) and 0.6 g of sulfolane were dissolved in 100 g of 1,2-dichloroethane. Aluminium chloride (37.0 g, mol) was added carefully in portions resulting in a red-orange mixture. A solution of dibenzodioxine (5.0 g, 0.03 mol) in 120 g of 1,2-dichloroethane was added within 1 hour. The resulting blue-violet mixture was stirred for 1.5 hours at 25° C. and was then poured into a stirred mixture of 150 g of ice, 100 g of water and 50 g of 32% hydrochloride acid.

The organic layer was separated, washed three times with water and dried over Na$_2$SO$_4$. The solvents were evaporated under vacuum yielding 11.4 g of the crude product which still contained residual sulfolane. By taking up the crude product in 1,2-dichloroacetate and washing twice with water (150 g and 80 g) the residual amounts of sulfolane were removed. The organic phase was dried over Na$_2$SO$_4$ and evaporated. The residue (11 g) was purified by column chromatography (100 g of silica gel, eluent: cyclohexane: ethyl acetate 4:1) to afford 6.0 g of compound 6 as yellowish crystals, mp 133-138° C.

$^1$H-NMR (400 MHz, CDCl$_3$), δ[ppm]: 1.44 (t, 6H), 4.46 (q, 4H), 6.99 (dd, 2H), 7.62 (s, 2H), 7.71 (d, 2H).
$^{13}$C-NMR (75.5 MHz, CDCl$_3$), δ[ppm]: 14.1, 62.5, 116.9, 118.1, 128.1, 129.1, 141.4, 146.9, 163.1, 183.6.
UV-Vis (ethyl acetate): $\lambda_{max}$=288 nm, 326 nm.

Example 7: Ethyl 2-[8-(2-ethoxy-2-oxo-acetyl)phenoxathiin-2-yl]-2-oxo-acetate (Compound 7)

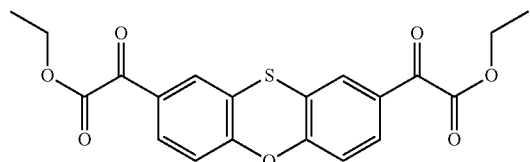

Compound 7 was prepared from phenothiazine in analogy to compound 1 in 2.3% yield. Brown-reddish, strong viscous oil.
$^1$H-NMR (400 MHz, CDCl$_3$), δ[ppm]: 1.45 (t, 6H), 4.67 (q, 4H), 7.11 (d, 2H), 8.10-8.15 (m, 4H).

Example 8: Ethyl 2-oxo-2-[8-(2-oxopentanoyl) dibenzofuran-2-yl]acetate (Compound 8)

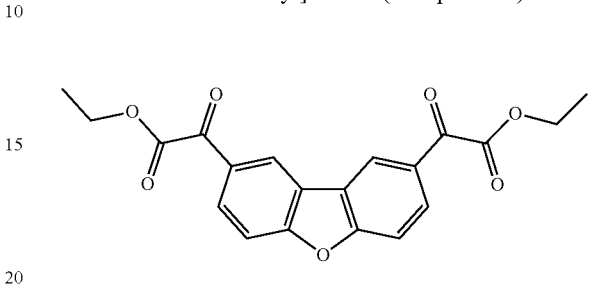

Compound 8 was prepared from dibenzofurane in analogy to compound 1. Colorless solid.
$^1$H-NMR (400 MHz, CDCl$_3$), λ[ppm]: 1.50 (t, 6H), 4.54 (q, 4H), 7.76 (d, 2H), 8.30 (d, 2H), 8.79 (s, 2H).
UV-Vis (Ethyl acetate): $\lambda_{max}$=257 nm and 287 nm.

Example 9: Ethyl 2-[9,9-dimethyl-7-(2-oxopentanoyl)fluoren-2-yl]-2-oxo-acetate (Compound 9)

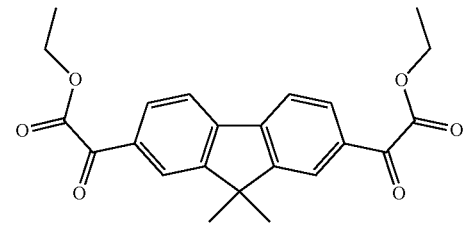 [SMILES: CCOC(=O)C(=O)c1ccc2c(c1)C(C)(C)c1cc(C(=O)C(=O)OCC)ccc1-2]

Dimethylfluorene (4.93 g, 26 mmol) and aluminium chloride (21.00 g, 154 mmol) were mixed in 200 g of 1,2-dichloroethane and 0.34 g of sulfolane. Ethyl chlorooxoacetate (19.36 g, 142 mmol) was added under stirring. The resulting black reaction mixture was stirred at room temperature. A TLC analysis after 2.5 hours indicated full conversion of dimethylfluorene. The reaction mixture was thereafter slowly poured into a stirred mixture of 300 g of ice/water. After addition of 50 mL of 1,2-dichloroethane and 1 L of water the organic layer was separated, dried over MgSO$_4$ and evaporated. The residue (9.27 g) was purified by column chromatographie (120 g silica gel, eluent 1: toluene/cyclohexane 7:3, eluent 2: toluene/ethyl acetate 9.5:1.5) yielding 4.5 g of the crude product. Another purification by column chromatography (65 g silica gel, eluent 1: toluene, eluent 2: toluene/ethyl acetate 9:1) was performed to yield 4.63 g of compound 9 as a dark yellow, very viscous oil.

$^1$H-NMR (400 MHz, CDCl$_3$), δ[ppm]: 1.46 (t, 6H), 1.61 (s, 6H), 4.51 (q, 4H), 7.93 (d, 2H), 8.05 (d, 2H), 8.17 (s, 2H).
UV-Vis (acetonitrile): $\lambda_{max}$=333 nm.

Example 10: Ethyl 2-oxo-2-[7-(2-oxopentanoyl)-9H-fluoren-2-yl]acetate (Compound 10)

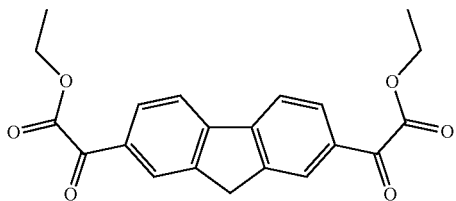 [SMILES: CCOC(=O)C(=O)c1ccc2c(c1)Cc1cc(C(=O)C(=O)OCC)ccc1-2]

Fluorene (15.00 g, 90 mmol) and sulfolane (1.16 g) were mixed in 100 mL of 1,2-dichloroethane. Aluminium chloride (42.20 g, 316 mmol) was added slowly under stirring. The resulting mixture was cooled to 0° C. Ethyl chlorooxoacetate (37.00 g, 271 mmol) was added within 90 minutes. The resulting red reaction mixture was stirred at room temperature for 24 hours. The reaction mixture was thereafter slowly poured onto ice and slowly warmed up to room temperature overnight. The organic layer was separated, washed three times with water and evaporated. The residue (9.27 g) was purified by flash chromatography (silica gel, eluent: hexane/ethylacetate 4:1) to afford 2.7 g of the title compound as a yellowish solid.

$^1$H-NMR (400 MHz, CDCl$_3$), λ[ppm]: 1.46 (t, 6H), 4.50 (q, 4H), 7.83 (d, 2H), 8.00 (d, 2H), 8.14 (s, 2H).

UV-Vis (acetonitrile): $\lambda_{max}$=335 nm.

Example 11: Ethyl 2-(9H-fluoren-2-yl)-2-oxo-acetate (Compound 11)

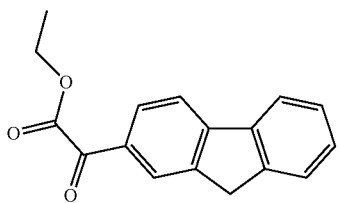 [SMILES: CCOC(=O)C(=O)c1ccc2c(c1)Cc1ccccc1-2]

Ethyl chlorooxoacetate (37.2 g, 270 mmol) and 1.10 g of sulfolane were mixed in 200 mL of 1,2-dichloroethane. Aluminium chloride (42.10 g, 316 mmol) was added at 5° C. slowly in portions. A solution of fluorene (15.0 g, 90 mmol) in 80 mL of 1,2-dichloroethane was added carefully. The resulting red mixture was stirred for 4.5 hours at 25° C. and was then poured into a stirred mixture of 100 g of ice, 150 g of water and 50 g of 32% hydrochloride acid.

The organic layer was separated, washed twice with water and dried over Na$_2$SO$_4$. The solvents were evaporated under vacuum. The residue (28.6 g) was purified by column chromatography (silica gel, heptane:ethyl acetate 9:1) to afford 18.4 g of the crude product. The crude product was further purified by column chromatography (silica gel, heptane/toluene 7:3) to afford 15 g of compound 11 as an off-white solid.

$^1$H-NMR (400 MHz, CDCl$_3$), δ[ppm]: 1.48 (t, 3H), 3.98 (s, 2H), 4.51 (q, 2H), 7.38-7.50 (m, 2H), 7.62 (d, 1H), 7.88 (d, 2H), 8.07 (d, 1H), 8.20 (s, 1H).

$^{13}$C-NMR (75.5 MHz, CDCl$_3$), δ[ppm]: 14.2, 37.0, 62.3, 120.0, 121.3, 125.4, 126.3, 127.2/128.7, 129.7, 130.8, 143.5, 144.7, 148.4, 164.3, 186.3.

UV-Vis (acetonitrile): $\lambda_{max}$=324 nm.

Example 12: Ethyl 2-dibenzofuran-2-yl-2-oxo-acetate (Compound 12)

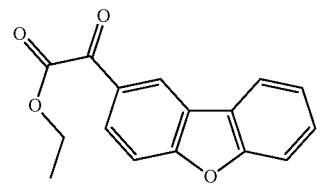 [SMILES: CCOC(=O)C(=O)c1ccc2oc3ccccc3c2c1]

Ethyl chlorooxoacetate (24.4 g, 270 mmol) and 1.0 g of sulfolane were mixed in 200 mL of 1,2-dichloroethane. Aluminium chloride (27.8 g, 316 mmol) was added at 0° C. slowly in portions. A solution of dibenzofurane (10.0 g, 90 mmol) in 50 mL of 1,2-dichloroethane was added carefully. The resulting red mixture was stirred for 1 hour at 5° C. and was then poured into a stirred mixture of 150 g of ice, 100 g of water and 50 g of 32% hydrochloride acid.

The organic layer was separated, washed twice with water and once with brine. The solvents were evaporated under vacuum. The residue was dissolved in ethyl acetate and the resulting organic phase was washed twice with water and once with brine. The solvents were evaporated under vacuum. The residue (13.5 g) was purified twice by column chromatography (column 1: silica gel, heptane:ethyl acetate 9:1; column 2: silica gel, heptane:toluene 7:3) to afford 3.9 g of the title compound as an off-white solid.

$^1$H-NMR (400 MHz, CDCl$_3$), δ[ppm]: 1.49 (t, 3H), 4.54 (q, 2H), 7.40-7.45 (m, 1H), 7.52-7.56 (m, 1H), 7.60-7.65 (m, 2H), 8.02 (d, 2H), 8.18 (d, 1H), 8.68 (s, 1H).

UV-Vis (acetonitrile): $\lambda_{max}$=260 nm, 276 nm, 312 nm (shoulder).

B) APPLICATION EXAMPLES

Materials
- photoinitiator Irgacure® 819 from BASF SE
- photoinitiator Irgacure® TPO from BASF SE
- photoinitiator Irgacure® TPO-L from BASF SE
- photoinitiator SpeedCure® CPTX from Lambson Ltd
- polymeric amine modified polyether acrylate Laromer® PO 9139 from BASF SE
- trifunctional monomer acrylate Laromer® LR 8863 from BASF SE
- substrate Melinex® 506 transparent polyester film with a thickness of 175 μm from DuPont Teijin Films
- spiral bar coater from BYK-Gardner GmbH for realizing a theoretical wet film thickness of 6 μm Equipment
- conveyor belt driven UV dryer from IST METZ GmbH equipped with a FirePower FP300 UV LED from Phoseon having an emission wavelength of 365 nm and an irradiance of 12 W/cm$^2$ (gap UV LED—substrate surface always adjusted to 10 mm)
- conveyor belt driven UV dryer from IST METZ GmbH equipped with a medium pressure mercury lamp M-300-U2H from IST METZ GmbH with an electrical input power of 200 W/cm
- colorimeter LICO 200 from Dr. Bruno Lange
- I.C.I. cone & plate viscometer from Research Equipment Ltd Test Methods
- reactivity was determined as the conveyor belt speed of the UV dryer, where immediately after UV curing under air the film could not be damaged anymore by scratching with a fingernail
- MEK (methyl ethyl ketone) resistance was determined for films 24 h after UV curing as the number of double rubs with a cotton pad soaked with MEK causing no visible damage of the film surface anymore
- viscosity was measured at 23.0° C. and a shear rate of 10000 sec$^{-1}$
- APHA color was evaluated by colorimetry Test Formulations

| Component | Test Formulation 1 | Test Formulation 2 | Test Formulation 3 | Test Formulation 4 | Test Formulation 5 | Test Formulation 6 |
|---|---|---|---|---|---|---|
| Laromer ® PO 9139 | 45.0% (w/w) | 45.0% (w/w) | 45.0% (w/w) | 45.0% (w/w) | 45.0% (w/w) | 45.0% (w/w) |
| Laromer ® LR 8863 | 50.0% (w/w) | 50.0% (w/w) | 51.5% (w/w) | 50.0% (w/w) | 49.0% (w/w) | 50.0% (w/w) |
| Irgacure ® TPO | 5.0% (w/w) | — | — | — | — | — |
| Irgacure ® TPO-L | — | 5.0% (w/w) | — | — | — | — |
| Irgacure ® 819 | — | — | 3.5% (w/w) | — | — | — |
| SpeedCure ® CPTX | — | — | — | 5.0% (w/w) | — | — |
| Example 11 | — | — | — | — | 5.0% (w/w) | — |
| Example 3 | — | — | — | — | — | 5.0% (w/w) |

Characterization of Test Formulations

| Test Formulation | Viscosity | APHA Color |
|---|---|---|
| 1 | 570 mPa · s | 369 |
| 2 | 580 mPa · s | 527 |
| 3 | 630 mPa · s | >900 |
| 4 | 580 mPa · s | >900 |
| 5 | 610 mPa · s | 711 |
| 6 | 700 mPa · s | 462 |

UV Reactivity and MEK Resistance of Test Formulations

| Test Formulation | Radiation Source | Reactivity | MEK Resistance |
|---|---|---|---|
| 1 | 365 nm UV LED | <3 m/min | — |
| 2 | 365 nm UV LED | <3 m/min | — |
| 3 | 365 nm UV LED | <3 m/min | — |
| 4 | 365 nm UV LED | 45 m/min | >200 double rubs |
| 5 | 365 nm UV LED | 10 m/min | >200 double rubs |
| 6 | 365 nm UV LED | 10 m/min | >200 double rubs |

The inventive photoinitiators of Example 11 and Example 3 are promoting proper surface cure under UV LED radiation along with thioxanthone and 4,4'-bis(dialkylamino)benzophenone derivatives being the only 2 commercially available photoinitiator classes up to now imparting surface cure under UV LED radiation. In contrast to that acylphosphine oxide photoinitiators known to provide through cure under UV LED radiation do not show any surface cure at all under the same conditions, even when corresponding prints were passed several times under the UV LED radiation source. These results were confirmed by MEK resistance tests, where the inventive photoinitiators resulted in excellent solvent resistance of the UV cured prints parallel to that of the thioxanthone and 4,4'-bis(dialkylamino)benzophenone ones.

| Test Formulation | Radiation Source | Reactivity | MEK Resistance |
|---|---|---|---|
| 1 | medium pressure mercury lamp | 65 m/min | >200 double rubs |
| 2 | medium pressure mercury lamp | 40 m/min | >200 double rubs |
| 3 | medium pressure mercury lamp | 40 m/min | >200 double rubs |
| 4 | medium pressure mercury lamp | 80 m/min | >200 double rubs |
| 5 | medium pressure mercury lamp | 80 m/min | >200 double rubs |
| 6 | medium pressure mercury lamp | 35 m/min | >200 double rubs |

The inventive photoinitiators of Example 11 and Example 3 are not only promoting proper surface cure under monochromatic UV LED radiation, but are also very reactive under a polychromatic medium pressure mercury lamp leading to excellent solvent resistance of corresponding UV cured prints as well.

Application Example in Photopolymer for 3D Printing

The inventive photoinitiators of Example 11 was tested at 1.5 wt-% in an acrylate-based photopolymer for 3D printing, e.g. stereolithography, consisting of two urethane acrylates and one monofunctional monomer. The polymerization heat and the glass transition temperature of the resulting polymer, shown in FIG. 1, were determined by means of photo-DSC and DSC (TGA/DSC 1, Mettler Toledo) after irradiation with a 365 nm LED (40 mW).

Test specimen (2 mm thickness) for determination of the mechanical properties (tensile test, DIN ISO 527-1, specimen type 5A, Zwick tensile testing equipment, speed 50 mm/min) of the cured polymer were prepared using homemade silicon molds in a two-step curing process: 1. pinning under UVA fluorescent tube (60 s, Sylvania Blacklight 368, F40W, T12, distance to sample 11 cm), 2. curing under 385 nm LED (two-sided curing, total UV dose 2500 mJ/cm$^2$). The determined values are shown in the table below.

| E modulus [MPa] | Stress at break [MPa] | Strain at break [%] |
| --- | --- | --- |
| 827 ± 112 | 27 | 39 |

The invention claimed is:

1. A photopolymerizable composition comprising:
(A) at least one ethylenically unsaturated photopolymerizable compound and
(B) at least one photoinitiator compound of formula (1)

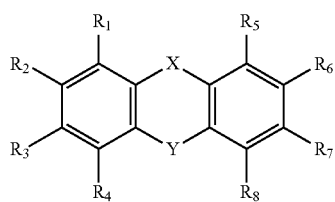

(1)

wherein
X is O, S or a direct bond;
Y is O, S or $CR_9R_{10}$;
$R_1$, $R_2$, $R_3$, $R_4$, $R_5$, $R_6$, $R_7$ and $R_8$ independently of each other are hydrogen, halogen, $C_1$-$C_{18}$alkyl, $C_5$-$C_{10}$cycloalkyl, $C_2$-$C_{18}$alkenyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (2)

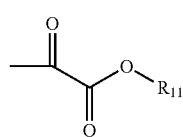

(2)

provided that one or more than one of $R_1$, $R_2$, $R_3$, $R_4$, $R_5$, $R_6$, $R_7$ or $R_8$ is a group of formula (2);
$R_9$, $R_{10}$ independently of each other are hydrogen, $C_1$-$C_{18}$alkyl, $C_2$-$C_{12}$alkenyl, $C_5$-$C_{10}$cycloalkyl, phenyl-$C_1$-$C_4$alkyl, phenyl or together with the C atom to which they are attached form a 5-membered, 6-membered or 7-membered ring; and
$R_{11}$ is hydrogen, $C_1$-$C_{18}$alkyl, $C_5$-$C_{10}$cycloalkyl, $C_2$-$C_{12}$alkenyl, phenyl, or phenyl-$C_1$-$C_4$alkyl.

2. The photopolymerizable composition according to claim 1, wherein the photoinitiator of formula (1) is a compound of formula (3):

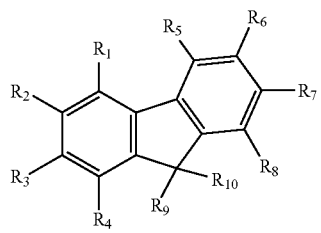

(3)

wherein;
$R_1$, $R_2$, $R_3$, $R_4$, $R_5$, $R_6$, $R_7$, $R_8$, $R_9$, and $R_{10}$ are as defined in claim 1.

3. The photopolymerizable composition according to claim 1, wherein:
(i) one of $R_1$, $R_2$, $R_3$, $R_4$, $R_5$, $R_6$, $R_7$ or $R_8$ is a group of formula (2);
or
(ii) one of $R_1$, $R_2$, $R_3$ or $R_4$ is a group of formula (2) and one of $R_5$, $R_6$, $R_7$ or $R_8$ is a group of formula (2).

4. The photopolymerizable composition according to claim 1, wherein $R_1$ to $R_4$ and $R_5$ to $R_8$ are independently of each other hydrogen, halogen, $C_1$-$C_4$alkyl, $C_1$-$C_4$alkoxy, $C_1$-$C_4$alkylthio, N-morpholinyl or N-piperidinyl or a group of formula (2).

5. The photopolymerizable composition according to claim 1, which additionally to the component (B) comprises:
(x) at least one further photoinitiator (C);
(xi) at least one further coinitiator (D);
(xii) at least one other additive (E); or
(xiii) a combination of (x) and (xi) or a combination of (x) and (xii) or a combination of (x) and (xi) and (xii).

6. The photopolymerizable composition according to claim 1, which comprises 0.05 to 15% by weight, of the photoinitiator compound of formula (1), based on the total composition.

7. A process for the photopolymerization of monomeric, oligomeric or polymeric compounds containing at least one ethylenically unsaturated double bond, which comprises:
adding to the monomeric, oligomeric or polymeric compounds at least one photoinitiator of formula (1);

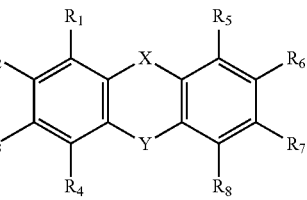

(1)

wherein;
X is O, S or a direct bond;
Y is O, S or $CR_9R_{10}$;
$R_1$, $R_2$, $R_3$, $R_4$, $R_5$, $R_6$, $R_7$ and $R_8$ independently of each other are hydrogen, halogen, $C_1$-$C_{18}$alkyl, $C_5$-$C_{10}$cycloalkyl, $C_2$-$C_{18}$alkenyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (2)

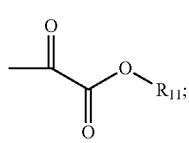

(2)

provided that one or more than one of $R_1$, $R_2$, $R_3$, $R_4$, $R_5$, $R_6$, $R_7$ or $R_8$ is a group of formula (2);
$R_9$, $R_{10}$ independently are hydrogen, $C_1$-$C_{18}$alkyl, $C_2$-$C_{12}$alkenyl, $C_5$-$C_{10}$cycloalkyl, phenyl-$C_1$-$C_4$alkyl, phenyl or together with the C atom to which they are attached form a 5-membered, 6-membered or 7-membered ring; and $R_{11}$ is hydrogen, $C_1$-$C_{18}$alkyl, $C_5$-$C_{10}$cycloalkyl, $C_2$-$C_{12}$alkenyl, phenyl, or phenyl-$C_1$-$C_4$alkyl; and irradiating the resulting composition with electromagnetic or particulate radiation.

8. The process according to claim 7, wherein the at least one photoinitiator of formula (1) is a compound of formula (3):

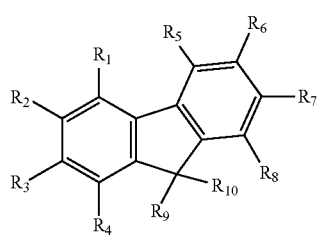

(3)

wherein;

$R_1$, $R_2$, $R_3$, $R_4$, $R_5$, $R_6$, $R_7$, $R_8$, $R_9$, and $R_{10}$ are as defined in claim 7.

9. The process according to claim 7, wherein the monomeric, oligomeric or polymeric compounds and the at least one photoinitiator are provided in a preparation of pigmented and nonpigmented paints and varnishes, powder coatings, printing inks, screen printing inks, inks for offset-, flexo- or inkjet printing, printing plates, adhesives, sealings, potting components, dental compositions, foams, moulding compounds, composite compositions, glass fibre cable coatings, screen printing stencils, compositions for producing three-dimensional objects by means of stereolithography, image recording material, photoresist compositions, decolorizing materials, decolorizing materials for image recording materials, or image recording materials using microcapsules.

10. A coated substrate coated on at least one surface with a composition according to claim 1.

11. Article comprising a polymerized or crosslinked composition obtained by curing a polymerizable composition according to claim 1.

12. The photopolymerizable composition according to claim 2, wherein $R_9$, and $R_{10}$ independently are hydrogen, $C_1$-$C_{18}$alkyl or together with the C atom to which they are attached form a 5-membered, 6-membered or 7-membered ring; and $R_{11}$ is $C_1$-$C_{18}$alkyl.

13. The photopolymerizable composition according to claim 2, wherein;

$R_9$, $R_{10}$ independently are hydrogen or methyl; and $R_{11}$ is methyl or ethyl.

14. The photopolymerizable composition according to claim 3, wherein;

$R_1$ to $R_4$ and $R_5$ to $R_8$ are independently a group of formula (2) or hydrogen.

15. The photopolymerizable composition according to claim 6, which comprises 0.1 to 10% by weight of the photoinitiator compound of formula (1).

16. The process according to claim 8, wherein;

(i) one of $R_1$, $R_2$, $R_3$, $R_4$, $R_5$, $R_6$, $R_7$ or $R_8$ is a group of formula (2); or (ii) one of $R_1$, $R_2$, $R_3$ or $R_4$ is a group of formula (2) and one of $R_5$, $R_6$, $R_7$ or $R_8$ is a group of formula (2).

17. The process according to claim 8, wherein $R_1$ to $R_4$ and $R_5$ to $R_8$ are independently of each other hydrogen, halogen, $C_1$-$C_4$alkyl, $C_1$-$C_4$alkoxy, $C_1$-$C_4$alkylthio, N-morpholinyl or N-piperidinyl or a group of formula (2).

* * * * *